United States Patent [19]

Brouard et al.

[11] 4,218,369
[45] Aug. 19, 1980

[54] CYCLOAMMONIUM-AZO-PHENYL-DYESTUFFS CONTAINING ONE CYANOETHYL, CARBAMOYLETHYL OR CARBALKOXYETHYL GROUP ON THE PHENYL RADICAL

[75] Inventors: Claude M. H. E. Brouard, St. Pierre les Elbeuf; Claude L. E. Moerel, Bihorel; Jean-Pierre H. Stiot, St. Pierre les Elbeuf, all of France

[73] Assignee: Produits Chimiques Ugine Kuhlmann, Paris, France

[21] Appl. No.: 838,326

[22] Filed: Sep. 30, 1977

[30] Foreign Application Priority Data

Oct. 12, 1976 [FR] France ................ 76 30580

[51] Int. Cl.² .............. C09B 29/08; D06P 3/24; D06P 3/52; D06P 3/76
[52] U.S. Cl. ................ 260/157; 260/146 R; 260/154; 260/158; 260/162; 260/163; 260/465 E; 260/465 G; 260/558 A; 260/578; 560/20
[58] Field of Search ............. 260/146 R, 147, 155, 260/156, 157, 158, 162, 163

[56] References Cited

U.S. PATENT DOCUMENTS 3,763,140 10/1973 Entschel et al. .............. 260/163

FOREIGN PATENT DOCUMENTS

| 2142565 | 3/1973 | Fed. Rep. of Germany | 260/158 |
| 1199751 | 12/1959 | France | 260/205 |
| 1205351 | 2/1960 | France | 260/205 |
| 1540834 | 8/1968 | France | 260/158 |
| 1220852 | 1/1971 | United Kingdom | 260/158 |

Primary Examiner—Floyd D. Higel
Attorney, Agent, or Firm—Beveridge, DeGrandi, Kline & Lunsford

[57] ABSTRACT

The invention relates to new cationic azo dyestuffs which correspond to the general formula:

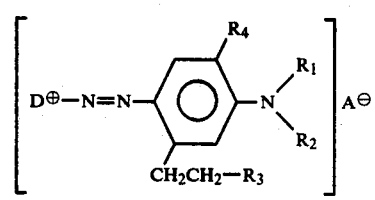

in which $R_1$ represents an alkyl radical or a substituted alkyl radical, $R_2$ represents a hydrogen atom, an alkyl radical or a substituted alkyl radical, $R_3$ represents a cyano, carbamoyl or carbalkoxy radical, $R_4$ represents a hydrogen or halogen atom or an alkyl or alkoxy radical, $D\oplus$ represents a cycloammonium radical and $A\ominus$ represents an anion. These dyestuffs are very suitable for dyeing and printing textile materials based on polymers or copolymers of unsaturated nitriles or on acid-modified polyesters or polyamides, in shades very fast to light and wet treatments.

5 Claims, No Drawings

CYCLOAMMONIUM-AZO-PHENYL-DYESTUFFS CONTAINING ONE CYANOETHYL, CARBAMOYLETHYL OR CARBALKOXYETHYL GROUP ON THE PHENYL RADICAL

BACKGROUND OF THE INVENTION

1. Field of the Invention

The present invention relates to new cationic azo dyestuffs especially useful for the coloration of acrylic fibers.

2. Description of the Prior Art

Numerous cationic azo dyestuffs of the diazahemicyanine type are already known (cf. K. Venkataraman "The Chemistry of Synthetic Dyes", Vol. IV, 1971, pages 188-201). These dyestuffs, which may be represented by the general formula:

$$[D^{\oplus}-N=N-B]A^{\ominus} \qquad (I)$$

in which $D^{\oplus}$ represents a cycloammonium radical, B represents the residue of an aromatic coupling components such as a secondary or tertiary benzene amine, a phenol or a compound with an active methylene group, and $A^{\ominus}$ represents an anion, may be prepared by the oxidizing coupling of a nitrogen-containing heterocyclic hydrazine with a coupling compound or by quaternization with an alkylating agent of an azo compound resulting from the coupling of the diazo compound of a heterocyclic amine with a coupling compound.

SUMMARY OF THE INVENTION

It has now been found by applicants that valuable cationic azo dyestuffs of the above type are obtained when there is used as coupling compound a compound of the formula:

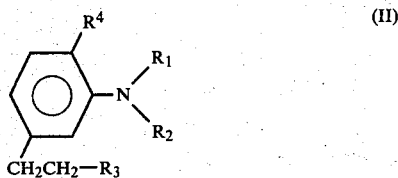

(II)

in which $R_1$ represents an alkyl radical or an alkyl radical substituted by a halogen atom or by a hydroxy, cyano, alkoxy or acyloxy group, $R_2$ represents a hydrogen atom, an alkyl radical or an alkyl radical substituted by a halogen atom or by a hydroxy, cyano, alkoxy or acyloxy group, $R_3$ represents a cyano, carbamoyl or carbalkoxy radical, and $R_4$ represents a hydrogen or halogen atom or an alkyl or alkoxy radical.

The alkyl or alkoxy radicals may contain 1 to 4 carbon atoms and are preferably those containing 1 or 2 carbon atoms. The halogen which may be substituted on $R_1$ and/or $R_2$ or which may be represented by $R_4$ is preferably chlorine or bromine. The acyloxy group which may be substituted on $R_1$ and/or $R_2$ may contain 2 to 5 carbon atoms and is preferably acetoxy or propionyloxy. When $R_3$ represents a carbalkoxy radical, this may contain 2 to 5 carbon atoms and is preferably a carbomethoxy or carbethoxy radical.

DESCRIPTION OF THE PREFERRED EMBODIMENTS

The invention has therefore as a primary object, new cationic azo dyestuffs corresponding to the general formula:

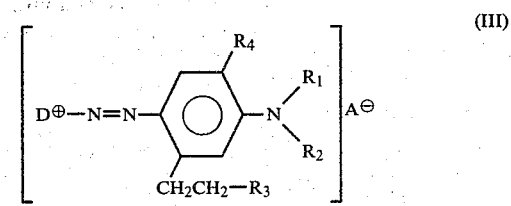

(III)

in which $R_1$, $R_2$, $R_3$, $R_4$, $D^{\oplus}$ and $A^{\ominus}$ have the same significance as above.

By the cycloammonium ($D^{\oplus}$) radical is meant a pentagonal or hexagonal heterocyclic radical comprising an atom of quaternary nitrogen and possibly one or two supplementary hetero-atoms such as sulfur, oxygen and nitrogen. The heterocyclic nucleus may be fused with one or several benzene nuclei. As examples of cycloammonium radicals may be mentioned more particularly the pyridinium, quinolinium, thiazolium, benzisothiazolium, benzimidazolium, oxadiazolium, thiadiazolium and isothiazolium radicals and above all the pyrazolium, triazolium, benzo-thiazolium and indazolium radicals. These radicals may carry one, two or three (preferably one or two) nonionic substituents such as halogen atoms (preferably chlorine or bromine), the nitro, cyano, alkyl carrying 1 to 4, preferably 1 or 2 carbon atoms, alkoxy carrying 1 to 4, preferably 1 or 2 carbon atoms, acylamino (especially the alkylcarbonylamino, alkylsulfonylamino, benzoylamino and phenylsulfonylamino groups, wherein the alkyl radical carries 1 to 4, preferably 1 or 2 carbon atoms and may be substituted, as may the phenyl radical of the benzoylamino and phenylsulfonylamino groups, by halogen atoms or hydroxy or cyano groups), sulfonamido or carbonamido as such or substituted on the nitrogen by one or two alkyl groups carrying 1 to 4, preferably 1 or 2 carbon atoms, carbalkoxy carrying 2 to 5 carbon atoms (in particular carbomethoxy or carbethoxy), acyloxy (in particular alkylcarbonyloxy groups of which the alkyl radical carries 1 to 4, preferably 1 or 2 carbon atoms), acyl (in particular the alkylcarbonyl and alkylsulfonyl groups wherein the alkyl radical carries 1 to 4, preferably 1 or 2 carbon atoms), aryl or substituted aryl (especially phenyl as such or substituted by an atom of halogen, preferably chlorine or bromine, a nitro group or an alkoxy group carrying 1 or 2 carbon atoms).

The coloration is conferred by the dyestuff cation. The anion $A^{\ominus}$ does not play any tinctorial role; it may be exchanged, if desired, with another anion, for example with a view to modifying the solubility of the dyestuffs. As examples of anions $A^{\ominus}$ may be mentioned those arising from the process of preparation, especially the halide anions (chloride, bromide, iodide), hydrogen sulfate, sulfate, sulfomethylate and arylsulfonate (e.g., benzenesulfonate, p-toluenesulfonate), as well as those arising from a subsequent change, especially the phosphate, acetate, oxalate, lactate and tartrate anions, or arising from the isolation of the dyestuffs in the form of their double salts with zinc or cadmium halides.

The dyestuffs of formula (III) according to the invention are preferably prepared by coupling the diazo derivative of a heterocyclic amine of the formula:

D—NH₂ (IV)

in which D represents a heterocyclic radical comprising at least one cyclic nitrogen atom, with a coupling compound of formula (II), the quaternization of the monoazo compound obtained of the formula:

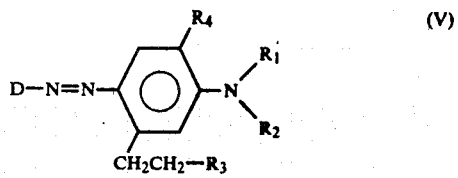

The diazotization of the amine of formula (IV) and the coupling of its diazo derivative with the coupling compound of formula (II) may be carried out in a known manner. The diazotization may be effected, for example, by means of a mineral acid and sodium nitrite or by means of a solution of nitrosylsulfuric acid in concentrated sulfuric acid, at a temperature between −10° and +40° C., preferably between −10° and +5° C. The coupling is generally carried out in an acid medium which may be buffered, at a temperature between −10° and +40° C., preferably between 0° and 5° C. Sodium acetate is generally used as the buffer.

The quaternization of the azo compound of formula (V) may be effected in a known way by heating for from 1 to 24 hours at a temperature of from 20° to 130° C., preferably from 75° to 130° C., and possibly under pressure, a mixture of the azo compound and a quaternization agent of the formula:

A′—X (VI)

in which A′ represents a splittable group in the form of anion A⊖ and X represents alkyl containing 1 to 4, preferably 1 or 2 carbon atoms, cycloalkyl containing 5 to 7 carbon atoms (preferably cyclohexyl), aralkyl (especially phenylalkyl or naphthylalkyl containing 1 to 4, preferably 1 or 2 carbon atoms in the alkyl residue), alkenyl or alkynyl containing up to 5 carbon atoms (preferably allyl or 2-propynyl). The reaction is effected in an inert solvent such as, for example, benzene, chloroform, dioxan, toluene, nitrobenzene, chlorobenzene, acetone or dimethylformamide and, preferably, also in the presence of an agent for fixing an acid such as, for example, magnesium oxide, calcium or sodium bicarbonate or magnesium carbonate. The alkylation may also be effected in the absence of organic solvent by using an excess of quaternizing agent. In some cases, the alkylation may also be effected in water. One or more X groups are introduced into the molecule of the dyestuff depending on the number of nitrogen atoms capable of being alkylated contained in the molecule of the azo compound of formula (V).

Examples of quaternizing agents (VI) are more especially halides such as methyl iodide, ethyl bromide, cyclohexyl chloride and benzyl bromide, sulfates such as dimethyl and diethyl sulfates, arylsulfonic esters such as methyl and benzyl p-toluenesulfonates. Other examples of quaternizing agents are bromopropionamide and bromopropionitrile.

The alkylation of the monoazo compounds of formula (V) may also be effected successfully by reacting with acrylic acid or its derivatives, for example acrylamide, in the presence of an organic or mineral acid, such as acetic, formic or hydrochloric acids or a mixture thereof at a temperature between 50° and 100° C.

The quaternization may also be effected by the action of ethylene oxide or an epoxide of the formula:

in which R₅ represents a hydrogen atom or a methyl radical and R₆ represents a methyl, ethyl, chloromethyl, methoxymethyl, ethoxymethyl, allyloxymethyl, phenoxymethyl or phenyl radical. This reaction is effected in a solvent medium in the presence of an organic or mineral acid which provides the anion A⊖ and at a temperature preferably between 40° and 90° C. Examples of suitable acids are sulfuric, phosphoric, hydrochloric, benzenesulfonic, toluenesulfonic, formic, acetic or propionic acid, the fatty acids being able to play simultaneously the role of solvent. Also suitable as solvents are, for example, dimethyl formamide, acetonitrile, dioxan, tetrahydrofuran, the benzene hydrocarbons and their halogenated derivatives, and nitrobenzene.

As examples of heterocyclic amines of formula (IV) may be mentioned the following compounds: 2-aminothiazole; 2-amino-4-methyl-thiazole; 2-amino-4-phenyl-thiazole; 2-amino-4-p-chlorophenyl-thiazole; 2-amino-4-p-nitrophenyl-thiazole; 2-amino-5-nitro-thiazole; 2-amino-4-methyl-5-nitro-thiazole; 2-amino-5-cyano-thiazole; 2-amino-5-mesyl-thiazole; 5-amino-3-methyl-isothiazole; 2-amino-benzothiazole; 2-amino-6-methyl-benzothiazole; 2-amino-6-methoxy-benzothiazole; 2-amino-6-chloro-benzothiazole; 2-amino-6-cyanobenzothiazole; 2-amino-6-nitro-benzothiazole; 2-amino-6-thiocyanatobenzothiazole; 2-amino-6-carbethoxy-benzothiazole; 2-amino-4-mesyl-benzothiazole; 2-amino-6-mesyl-benzothiazole; 3-amino-2,1-benzisothiazole; 3-amino-5-chloro-2,1-benzisothiazole; 3-amino-5-nitro-2,1-benzisothiazole; 3-amino-6-methyl-2,1-benzisothiazole; 3-amino-5-chloro-7-bromo-2,1-benzisothiazole; 3-amino-5-nitro-7-chloro-2,1-benzisothiazole; 3-amino-5-nitro-7-bromo-2,1-benzisothiazole; 3-aminopyridine; 3-amino-quinoline; 8-amino-quinoline; 4-amino-8-methoxy-quinoline; 4-amino-8-ethoxy-quinoline; 8-amino-6-methoxy-quinoline; 2-amino-1,3,4-thiadiazole; 5-amino-1,2,4-thiadiazole; 5-amino-3-methyl-1,2,4-thiadiazole; 5-amino-3-phenyl-1,2,4-thiadiazole; 2-amino-5-phenyl-1,3,4-thiadiazole; 3-amino-pyrazole; 3-amino-1-phenylpyrazole; 3-amino-5-phenyl-pyrazole; 3-amino-4-cyano-pyrazole; 3-amino-1-(4-methoxyphenyl)-pyrazole; 5-amino-1-p-tolyl-3-methyl-pyrazole; 3-amino-indazole; 3-amino-5-nitro-indazole; 3-amino-6-chloro-indazole; 2-amino-benzimidazole; 3-amino-1,2,4-triazole; 3-amino-5-methyl-1,2,4-triazole; 3-amino-5-ethyl-1,2,4-triazole; 3-amino-5-phenyl-1,2,4-triazole; 3-amino-5-benzyl-1,2,4-triazole; 5-amino-tetrazole; 5-amino-6-methoxy-quinoxaline; 5-amino-3-methyl-1,2,4-oxadiazole. Of the dyestuffs of formula (III), those in which R₃ represents a cyano or carbalkoxy radical are preferred, in particular those which are derived from the heterocyclic amines of the formulae:

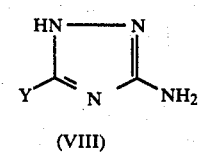 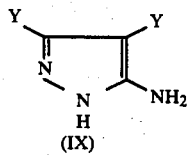

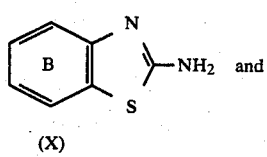 and 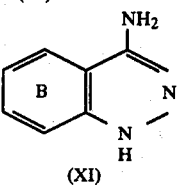

in which each Y represents a hydrogen atom or a nitro, cyano, alkoxy (with 1 to 4, preferably 1 or 2 carbon atoms), carbalkoxy (with 2 to 5, preferably 2 or 3 carbon atoms), an aryl group or substituted aryl group, (especially phenyl unsubstituted or substituted by one halogen, nitro, methoxy or ethoxy) and the benzene nuclei B may carry one or two nonionic substituents such as those previously disclosed.

The coupling compounds of formula (II) are new products. Their preparation forms the object of the concurrently filed copending application entitled "NEW N-SUBSTITUTED ANILINES" (Applicants: Paul M. C. Bourdauducq, Claude M. H. E. Brouard, Claude L. E. Moerel, and Jean-Pierre H. Stiot), Ser. No. 838,326 filed Sept. 30, 1977, the disclosure of which application is incorporated herein in its entirety by reference. They may be obtained according to known methods (Meerwein reaction, reduction, alkylation, hydrolysis, acylation, esterification) from m-nitranilines of the formula:

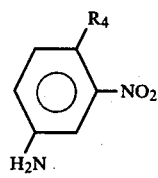

in which $R_4$ has the same significance as above.

A compound of the formula:

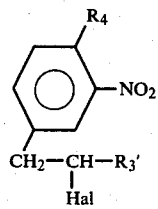

in which "Hal" denotes a halogen atom and $R'_3$ represents a cyano or carbalkoxy radical, is obtained according to the Meerwein reaction by the action of acrylonitrile or an alkyl acrylate on a diazonium halide of a m-nitraniline of formula (XII) in the presence of a copper salt as catalyst.

By reduction of the compounds of formula (XIII), anilines of the following formula are then formed:

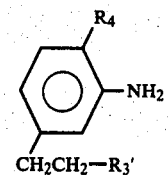

in which $R'_3$ and $R_4$ have the same significance as above.

On treatment of the anilines of formula (XIV) with an alkylating agent such as, for example, methyl or ethyl bromide, dimethyl or diethyl sulfate, glycol chlorhydrin, or acrylonitrile, coupling compounds according to the invention are obtained of the formula:

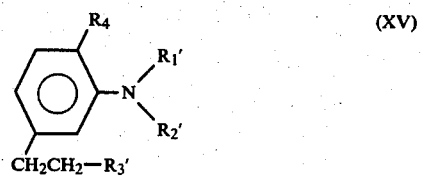

in which $R'_3$ and $R_4$ have the same significance as above, $R'_1$ represents an alkyl, hydroxyalkyl or cyanalkyl radical, and $R'_2$ represents a hydrogen atom or an alkyl, hydroxyalkyl or cyanalkyl radical, the alkyl components of $R'_1$ and $R'_2$ containing from 1 to 4 carbon atoms, preferably or 2 carbon atoms. The monoalkylation gives coupling compounds of the formula (XV) in which $R'_2$ is a hydrogen atom and the dialkylation to the coupling compounds of formula (XV) in which $R'_2$ is an alkyl, hydroxyalkyl or cyanalkyl radical. In order to obtain a coupling compound of formula (XV) in which $R'_1$ and $R'_2$ represent different radicals (for example $R'_1$=ethyl and $R'_2$=cyanethyl), it is sufficient to follow the monoalkylation with an alkylation by means of an alkylating agent different from that used for the monoalkylation.

The coupling compounds of formula (II) in which $R_3$ represents a carbamoyl radical, may be obtained by hydrolysis of the corresponding compounds of formula (II) in which $R_3$ represents a cyano radical.

The coupling compounds of formula (II) in which $R_1$ and/or $R_2$ represents an alkyl radical substituted by an alkoxy or acyloxy group may be prepared from coupling compounds of formula (II) in which $R_1$ and/or $R_2$ represents a hydroxyalkyl radical by etherification with an alcohol or by esterification with an acid chloride or anhydride.

The dyestuffs according to the invention are generally less sensitive to electrolytes and have for the most part a very good solubility in water and in polar solvents. They are very suitable for dyeing and printing of textile materials constituted entirely or predominantly of polymers or copolymers of unsaturated nitriles such as acrylonitrile and vinylidene cyanide or by polyesters or polyamides modified by an acid, in shades very fast to light and to wet treatments.

The dyeing with the dyestuffs according to the invention is generally effected in a neutral or acid aqueous medium, at the boiling point under atmospheric pressure or in a closed vessel at higher temperatures and at a greater pressure, e.g., temperatures of from 120° to 130° C. The presence of commercial levelling agents is not inconvenient, but it is not critical. The dyestuffs according to the invention are especially suitable also for three-color dyeing. In addition, on account of their fastness to hydrolysis, they can be used advantageously for dyeing at elevated temperature and dyeing in the presence of wool.

They can also be applied by printing. For this purpose, for example, a printing color containing the dyestuff and the auxiliary agents generally used in printing is employed. The dyestuffs according to the invention are also adapted to dyeing in bulk of polymers based on acrylonitrile or other possibly dissolved bulk plastics, in shades fast to light and to washing, as well as the coloration of oil paints or lacquers, and finally also for the dyeing of cotton, especially tanned cotton, and the dyeing of cellulose, regenerated cellulose and paper.

In the following Examples, to which the invention is not restricted, the parts and percentages are by weight, unless otherwise indicated. The parts by weight and the parts by volume are in the same relation as the gram and the milliliter.

PREPARATION OF THE COUPLING COMPOUNDS

EXAMPLE A

3-Diethylamino-hydrocinnamonitrile (or N,N-diethyl-3-β-cyanethyl-aniline)

(a) Meerwein reaction

An acid aqueous solution, freshly prepared, of the diazo compound from 138 parts of metanitraniline and a solution of 5 parts of cuprous chloride in 20 parts by volume of 19° Bé hydrochloric acid were introduced, run in in parallel, into a mixture of 50 parts by volume of glacial acetic acid, 100 parts by volume of acrylonitrile and 15 parts by volume of methylethylketone. The mixture was heated to 35°–40° C. and this temperature was maintained until the diazonium salt had disappeared (about 2 hours). After cooling and filtering, 180 parts of 2-chloro-3-(3-nitro-phenyl)-propanenitrile (M.P.=90° C.) were obtained of the formula:

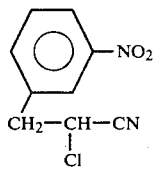

(b) Reduction 105 parts of 2-chloro-3-(3-nitro-phenyl)-propanenitrile were introduced in small amounts, while maintaining the temperature in the vicinity of 95° C., into 500 parts of boiling water, to which had been added 100 parts of iron powder and 6 parts by volume of glacial acetic acid. The mixture was then stirred under reflux for 1 to 2 hours. At the end of the reaction, followed by chromatography on a thin layer of silica, the mixture was extracted with 100 parts by volume of chlorobenzene, then neutralized with sodium hydroxide and the iron sludge was filtered off. After decantation and distillation of the chlorobenzene, 57 parts of crude 3-amino-hydrocinnamonitrile (or 3-β-cyanethyl-aniline) were obtained in the form of an oil which can be purified by subsequent distillation (B.P.=168° C./4 mm Hg).

(c) Alkylation 430 parts by volume of diethyl sulfate were introduced drop by drop into a mixture of 146 parts of 3-β-cyanethyl-aniline, 1000 parts of water and 233 parts of sodium carbonate. The mixture was heated to 40° C. and maintained at this temperature for about 12 hours. Then 1200 parts of water were added to the reaction mixture, which was then stirred for 30 minutes, then decanted.

220 parts of crude N,N-diethyl-3-β-cyanethyl-aniline were thus obtained of the formula:

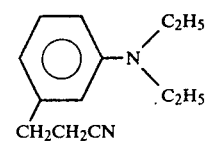

in the form of a brownish oil which may be purified by distillation (B.P.=142° C./3 mm Hg).

The retention time Tr of the N,N-diethyl-3-β-cyanethylaniline, measured at 220° C. on a Chromosorb W 15% SE 30 column of 1.5 m length and 2 mm interior diameter with an output of nitrogen of 25 ml/min., was 191 seconds.

EXAMPLE B

The operation was as in Example A, with the exception that the acrylonitrile was replaced by an equivalent molar amount of ethyl acrylate. N,N-diethyl-3-β-carbethoxyethyl-aniline (or ethyl 3-diethylaminohydrocinnamate) was thus obtained, the retention time Tr of which, measured as in Example A, was 251 seconds.

EXAMPLE C

3-N,N-bis-(β-hydroxyethyl)-amino-hydrocinnamonitrile

A mixture containing 100 parts of water, 100 parts of calcium carbonate, 160 parts of glycol chlorhydrin and 73 parts of 3-amino-hydrocinnamonitrile was heated under reflux for 29 hours. It was filtered hot and washed with hot water. After decantation, 103 parts of crude 3-N,N-bis-(β-hydroxyethyl)-amino-hydrocinnamonitrile were obtained of the formula:

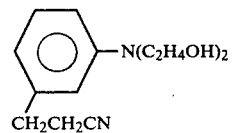

in the form of an oil which may be purified by distillation (Tr=898 s). The oil may be used directly without purification for the preparation of the dyestuffs.

EXAMPLE D

3-N,N-bis(β-acetoxyethyl)amino-hydrocinnamonitrile

A mixture of 52 parts of 3-N,N-bis(β-hydroxyethyl)aminohydrocinnamonitrile, 100 parts by volume of glacial acetic acid and 56 parts of acetic anhydride was refluxed for 8 hours. After distillation in vacuo, the 3-N,N-bis(β-acetoxyethyl)-amino-hydrocinnamonitrile was thus obtained of the formula:

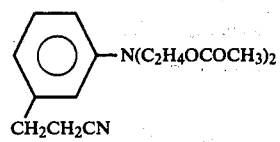

| Analysis | | | |
|---|---|---|---|
| | C% | H% | N% |
| Calculated for $C_{17}H_{22}N_2O_4$ | 64.1 | 6.92 | 8.80 |
| Found | 63.8 | 6.87 | 8.63 |

EXAMPLE E

3-N-ethylamino-hydrocinnamonitrile 143 parts by volume of diethyl sulfate were introduced drop by drop into a mixture of 146 parts of 3-amino-hydro-cinnamonitrile, 1000 parts of water and 160 parts of sodium carbonate. It was heated to about 30° C. and this temperature was maintained to the end of the reaction, easily followed by chromatography on a thin layer of silica. After decantation and distillation in vacuo, 140 parts of 3-N-ethylamino-hydro-cinnamonitrile were obtained which boiled at 153° C. under 2.5 mm of mercury and of which the retention time, measured as in Example A, was 154 seconds.

EXAMPLE F 3-(N-ethyl-N-β-cyanethyl-amino)-hydrocinnamonitrile

A mixture of 174 parts of 3-N-ethylamino-hydrocinnamonitrile, 250 parts by volume of glacial acetic acid and 64 parts of acrylonitrile was raised to 95° C. and allowed to react at 95° C. for about 24 hours. After distillation in vacuo, 3-(N-ethyl-N-β-cyanethyl-amino)-hydrocinnamonitrile was obtained of the formula:

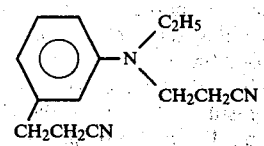

of which the retention time, measured as in Example A, was 552 seconds.

EXAMPLE G 3-(N-ethyl-N-β-hydroxyethyl-amino)-hydrocinnamonitrile

A mixture of 174 parts of 3-N-ethylamino-hydrocinnamonitrile, 330 parts of glycol chlorhydrin, 200 parts of water and 200 parts of calcium carbonate was heated under reflux for about 24 hours. The product was filtered hot, washed with 60 parts of hot water, decanted and distilled in vacuo. There were thus obtained 150 parts of 3-(N-ethyl-N-β-hydroxyethyl-amino)-hydrocinnamonitrile of the formula:

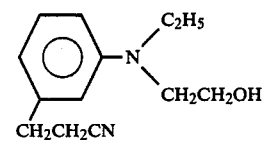

in the form of an oil which boiled at 205° C. under 2 mm of mercury.

EXAMPLE H 3-(N-ethyl-N-β-acetoxyethylamino)-hydrocinnamonitrile

A mixture of 218 parts of 3-(N-ethyl-N-β-hydroxyethylamino)-hydrocinnamonitrile, 100 parts by volume of glacial acetic acid and 115 parts by volume of acetic anhydride was heated under reflux for 4 hours. At the end of the reaction, easily followed by chromatography on a thin layer of silica, the product was neutralized with sodium carbonate and 200 parts were decanted of 3-(N-ethyl-N-β-acetoxyethyl-amino)-hydrocinnamonitrile of the formula:

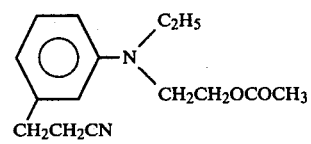

in the form of an oil which boiled at 192° C. under 20 mm of mercury.

Table I below tabulates other examples of coupling compounds of formula (II) prepared as in the preceding examples. The results of the elementary analyses of these products are according to theory.

TABLE I

| Ex. | $R_1$ | $R_2$ | $R_3$ | $R_4$ | Preparation according to the examples |
|---|---|---|---|---|---|
| J | $C_2H_5$ | $C_2H_5$ | CN | Cl | A |
| K | " | " | " | $CH_3$ | A |
| L | " | " | " | $OCH_3$ | A |
| M | " | " | " | $COOC_2H_5$ H | A |
| N | " | " | " | Cl | A |
| O | " | " | " | $CH_3$ | A |
| P | " | " | " | $OCH_3$ | A |
| Q | $CH_2CH_2OH$ | $CH_2CH_2OH$ | CN | Cl | Aa + Ab + C |
| R | " | " | " | $CH_3$ | " |
| S | " | " | " | $OCH_3$ | " |
| T | " | " | $COOC_2H_5$ | H | " |
| U | " | " | " | Cl | " |
| V | " | " | " | $CH_3$ | " |
| W | " | " | " | $OCH_3$ | " |
| X | $CH_2CH_2OCOCH_3$ | $CH_2CH_2OCOCH_3$ | CN | Cl | Aa + Ab + C + D |
| Y | " | " | " | $CH_3$ | " |
| Z | " | " | " | $OCH_3$ | " |

TABLE I-continued

| Ex. | R₁ | R₂ | R₃ | R₄ | Preparation according to the examples |
|---|---|---|---|---|---|
| AA | " | " | COOC₂H₅ | H | " |
| AB | " | " | " | Cl | " |
| AC | " | " | " | CH₃ | " |
| AD | " | " | " | OCH₃ | " |
| AE | C₂H₅ | CH₂CH₂CN | " | H | Aa + Ab + E + F |
| AF | " | " | " | CH₃ | " |
| AG | " | " | " | OCH₃ | " |
| AH | " | CH₂CH₂OH | CN | CH₃ | Aa + Ab + E + G |
| AI | " | CH₂CH₂OCOCH₃ | " | " | Aa + Ab + E + G + H |
| AJ | " | " | COOC₂H₅ | H | " |

EXAMMPLE AK

3-Diethylamino-hydrocinnamamide

A mixture of 40 parts of 3-diethylamino-hydrocinnamonitrile (A), 34 parts by volume of 66° Bé sulfuric acid and 6 parts of water was heated at 100°–105° C. for one hour. The reaction mixture was then left to cool to about 60° C., then poured onto 500 parts of ice. It was neutralized by addition of about 160 parts by volume of a 35° Bé solution of sodium hydroxide, while assuring that the temperature of the mixture did not exceed 20° C. After filtering and washing with water, 3-diethylamino-hydrocinnamamide was obtained of the formula:

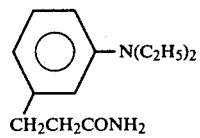

CH₂CH₂CONH₂ which melted at 59° C.

On operating as in the previous Example from 3-N,N-bis-(β-hydroxyethyl)amino-hydrocinnamonitrile (C), 3-[N,N-bis-(β-hydroxyethyl)amino]-hydrocinnamamide was obtained.

PREPARATION OF THE DYESTUFFS AND THEIR APPLICATION

EXAMPLE 1

72 parts of 2-amino-6-methoxy-benzothiazole were dissolved in a mixture of 480 parts by volume of glacial acetic acid and 240 parts of water. Then 120 parts by volume of 48% sulfuric acid were added, and then the amount of nitrosylsulfuric acid corresponding to 27.6 parts of sodium nitrite was slowly introduced with stirring and at a temperature between $-5°$ and $-10°$ C. After a further hour of stirring at this temperature, the excess nitrous acid was destroyed by addition of sulfamic acid. Then the diazo compound thus formed was poured onto a mixture of 86 parts of N,N-diethyl-3-β-cyanethyl-aniline (A), 80 parts by volume of 48% sulfuric acid, 200 parts of water and 1000 parts of ice. After 2 hours stirring, the mixture was filtered, then the solid product was taken up in 2,000 parts of water. The suspension thus obtained was then neutralized by addition of about 200 parts by volume of a 20% solution of sodium hydroxide, then filtered. 126 parts of 6-methoxy-2-(2-β-cyanethyl-4-diethylamino-phenylazo)-benzothiazole were thus isolated.

40 parts of this monoazo compound were made into a paste in 150 parts of water, the 42.5 parts of sodium bicarbonate and 63 parts of dimethyl sulfate were added at ambient temperature. The evolution of the reaction was followed by chromatography on thin layers of silica. After 8 hours stirring at ambient temperature, filtration, draining and drying at 60° C., 53 parts of the dyestuff corresponding to the following formula were obtained:

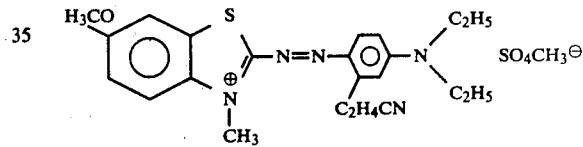

The dyestuff has a remarkable affinity for textile materials capable of being dyed by cationic dyestuffs, especially those based on polyacrylonitrile, which it dyes in a very full-bodied blue shade which is remarkably fast to light and moisture.

The following Table II tabulates other Examples of dyestuffs according to the invention prepared as in Example 1 by coupling the diazo derivative of the amine D-NH₂ indicated in the second column with the coupling compound of formula (II) in which the symbols R₁, R₂, R₃ and R₄ have the significance indicated in the third, fourth, fifth and sixth columns of the table, then quaternization of the monoazo compound thus obtained with the alkylating agent indicated in the seventh column, in the presence of an acid accepter.

TABLE II

| Ex. | Amine D—NH₂ | Coupling compound of formula (II) | | | | Alkylating agent | Shades on P.A.N |
|---|---|---|---|---|---|---|---|
| | | R₁ | R₂ | R₃ | R₄ | | |
| 2 | 2-amino-6-methoxy-benzothiazole | C₂H₅ | C₂H₅ | CN | Cl | SO₄(CH₃)₂ | blue |
| 3 | 2-amino-6-methoxy-benzothiazole | " | " | CN | CH₃ | " | " |
| 4 | 2-amino-6-methoxy-benzothiazole | " | " | CN | OCH₃ | " | green-blue |
| 5 | 2-amino-6-methoxy-benzothiazole | " | " | COOC₂H₅ | H | " | green-blue |
| 6 | 2-amino-6-methoxy- | " | " | " | Cl | " | green- |

TABLE II-continued

| Ex. | Amine D—NH$_2$ | Coupling compound of formula (II) R$_1$ | R$_2$ | R$_3$ | R$_4$ | Alkylating agent | Shades on P.A.N |
|---|---|---|---|---|---|---|---|
| | benzothiazole | | | | | | blue |
| 7 | 2-amino-6-methoxy-benzothiazole | " | " | " | CH$_3$ | " | green-blue |
| 8 | 2-amino-6-methoxy-benzothiazole | C$_2$H$_4$OH | C$_2$H$_4$OH | CN | H | " | blue |
| 9 | 2-amino-6-methoxy-benzothiazole | " | " | COOC$_2$H$_5$ | H | " | green-blue |
| 10 | 2-amino-6-methoxy-benzothiazole | C$_2$H$_4$OCOCH$_3$ | C$_2$H$_4$OCOCH$_3$ | " | H | " | green-blue |
| 11 | 2-amino-6-methoxy-benzothiazole | " | " | CN | H | " | blue |
| 12 | 2-amino-6-methoxy-benzothiazole | C$_2$H$_5$ | C$_2$H$_4$OH | CN | H | " | green-blue |
| 13 | 2-amino-6-methoxy-benzothiazole | " | C$_2$H$_4$OCOCH$_3$ | CN | H | " | green-blue |
| 14 | 2-amino-6-methoxy-benzothiazole | " | C$_2$H$_4$CN | CN | H | " | green-blue |
| 15 | 2-amino-6-methoxy-benzothiazole | " | C$_2$H$_5$ | CN | H | SO$_4$(C$_2$H$_5$)$_2$ | blue |
| 16 | 2-amino-6-methoxy-benzothiazole | " | " | CN | H | ethylene oxide | " |
| 17 | 2-amino-6-ethoxy-benzothiazole | " | " | CN | Cl | SO$_4$(CH$_3$)$_2$ | " |
| 18 | 2-amino-6-ethoxy-benzothiazole | C$_2$H$_4$OH | C$_2$H$_4$OH | COOC$_2$H$_5$ | H | " | " |
| 19 | 2-amino-6-ethoxy-benzothiazole | " | " | CONH$_2$ | H | " | " |
| 20 | β-acetoxyethyl ester of 2-amino-benzothiazole-6-carboxylic acid | C$_2$H$_5$ | C$_2$H$_5$ | CN | H | " | blue-violet |
| 21 | β-acetoxyethyl ester of 2-amino-benzothiazole-6-carboxylic acid | " | " | COOC$_2$H$_5$ | H | " | blue-violet |
| 22 | β-acetoxyethyl ester of 2-amino-benzothiazole-6-carboxylic acid | C$_2$H$_4$OH | C$_2$H$_4$OH | " | H | " | blue-violet |
| 23 | β-acetoxyethyl ester of 2-amino-benzothiazole-6-carboxylic acid | C$_2$H$_5$ | C$_2$H$_4$CN | " | H | " | blue-violet |
| 24 | β-acetoxyethyl ester of 2-amino-benzothiazole-6-carboxylic acid | " | C$_2$H$_4$OCOCH$_3$ | CN | H | " | blue-violet |
| 25 | β-acetoxyethyl ester of 2-amino-benzothiazole-6-carboxylic acid | " | " | CN | H | SO$_4$(C$_2$H$_5$)$_2$ | blue-violet |
| 26 | 2-amino-6-nitro-benzothiazole | " | C$_2$H$_5$ | CN | H | SO$_4$(CH$_3$)$_2$ | violet |
| 27 | 2-amino-6-nitro-benzothiazole | " | " | COOC$_2$H$_5$ | H | " | blue-violet |
| 28 | 2-amino-6-nitro-benzothiazole | C$_2$H$_4$OH | C$_2$H$_4$OH | CONH$_2$ | H | " | blue-violet |
| 29 | 3-amino-5-nitro-indazole | C$_2$H$_5$ | C$_2$H$_5$ | CN | H | SO$_4$(CH$_3$)$_2$ | blue |
| 30 | 3-amino-5-nitro-indazole | C$_2$H$_4$OH | C$_2$H$_4$OH | CN | H | " | " |
| 31 | 3-amino-5-nitro-indazole | C$_2$H$_4$OCOCH$_3$ | C$_2$H$_4$OCOCH$_3$ | CN | H | " | " |
| 32 | 3-amino-5-nitro-indazole | C$_2$H$_5$ | C$_2$H$_4$CN | CN | H | " | " |
| 33 | 3-amino-5-nitro-indazole | " | C$_2$H$_4$OH | CN | H | " | " |
| 34 | 3-amino-5-nitro-indazole | " | C$_2$H$_4$OCOCH$_3$ | CN | H | " | " |
| 35 | 3-amino-5-nitro-indazole | " | C$_2$H$_4$CN | COOC$_2$H$_5$ | CH$_3$ | SO$_4$(C$_2$H$_5$)$_2$ | " |
| 36 | 6-amino-indazole | " | C$_2$H$_5$ | CN | H | SO$_4$(CH$_3$)$_2$ | red |
| 37 | " | " | " | CN | Cl | " | " |
| 38 | " | " | " | CN | CH$_3$ | " | " |
| 39 | " | " | " | CN | OCH$_3$ | " | " |
| 40 | " | C$_2$H$_4$OH | C$_2$H$_4$OH | COOC$_2$H$_5$ | H | SO$_4$(C$_2$H$_5$)$_2$ | " |
| 41 | 3-amino-1,2,4-triazole | C$_2$H$_5$ | C$_2$H$_5$ | CN | H | SO$_4$(CH$_3$)$_2$ | " |
| 42 | 3-amino-1,2,4- | C$_2$H$_4$OH | C$_2$H$_4$OH | CN | H | " | " |

TABLE II-continued

| Ex. | Amine D—NH$_2$ | R$_1$ | R$_2$ | R$_3$ | R$_4$ | Alkylating agent | Shades on P.A.N |
|---|---|---|---|---|---|---|---|
| 43 | 3-amino-1,2,4-triazole | C$_2$H$_5$ | C$_2$H$_4$CN | CN | H | " | " |
| 44 | 3-amino-1,2,4-triazole | " | C$_2$H$_4$OH | CN | H | " | " |
| 45 | 3-amino-1,2,4-triazole | " | C$_2$H$_4$OCOCH$_3$ | CN | H | " | " |
| 46 | 3-amino-1,2,4-triazole | " | " | CN | CH$_3$ | " | " |
| 47 | 3-amino-1,2,4-triazole | " | C$_2$H$_5$ | COOC$_2$H$_5$ | H | " | " |
| 48 | 5-amino-3-phenyl-pyrazole | " | " | " | H | " | scarlet red |
| 49 | 5-amino-3-phenyl-pyrazole | " | " | CN | H | " | scarlet red |
| 50 | 5-amino-3-phenyl-pyrazole | " | " | CN | OCH$_3$ | " | scarlet red |
| 51 | 5-amino-3-phenyl-pyrazole | C$_2$H$_4$OH | C$_2$H$_4$OH | CN | " | " | scarlet red |
| 52 | 5-amino-4-chloro-3-phenyl-pyrazole | C$_2$H$_5$ | C$_2$H$_5$ | CN | H | " | scarlet red |
| 53 | 5-amino-4-chloro-3-phenyl-pyrazole | C$_2$H$_4$OH | C$_2$H$_4$OH | CN | OCH$_3$ | " | scarlet red |
| 54 | 5-amino-4-chloro-3-phenyl-pyrazole | C$_2$H$_5$ | C$_2$H$_4$CN | COOC$_2$H$_5$ | " | " | violet-red |
| 55 | 5-amino-4-chloro-3-phenyl-pyrazole | " | C$_2$H$_5$ | " | H | " | red |

EXAMPLE 56

The dyestuff obtained from Example 1 (sulfomethylate) was dissolved in 500 parts of water. Sodium chloride and a solution of zinc chloride were added, then the solid was filtered off and dried, the dyestuff of the following formula being obtained:

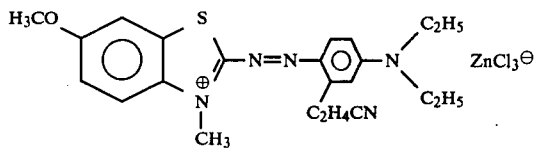

which dyed polyacrylonitrile textile goods in a deep blue shade which was very fast to light and to wetting.

On operation in an analogous way, the dyestuffs described in Examples 2 to 55 were converted into double salts derived from zinc chloride.

EXAMPLE 57

A paste was formed with 0.1 parts of the dyestuff described in Example 1, about 2 parts of water and possibly a little acetic acid, then this paste was dissolved in 50 parts of hot water. Then 0.5 to 2 parts of Unisol T (product of condensation of oleylamine with ethylene oxide) were added and the solution was made up to 500 parts by addition of cold water. The pH of the dyebath was adjusted to 4.5 to 5 by addition of acetic acid or sodium acetate.

10 parts of polyacrylonitrile fibers or polyamide fibers modified by an acid were kept moving in this dyebath while its temperature was raised to 100° C. in 30 minutes. It was kept at the boil for an hour, then the fibers were rinsed in cold water and dried at 60° to 70° C.

Fibers of ethylene glycol polyterephthalate modified by an acid, such as Dacron 64, may be dyed in the same way, but 1 to 3 parts of a carrier such as, for example, a benzene or diphenyl-hydroxycarboxylic acid ester are added to the dyebath.

EXAMPLE 58

330 parts of hot water were poured on a mixture of 30 parts of the dyestuff described in Example 1, 50 parts of thiodiethylene glycol, 30 parts of cyclohexanol and 30 parts of 30% acetic acid. The solution thus obtained was added to 500 parts of gum crystal (gum arabic as thickener), then 30 parts of a solution of zinc nitrate (d=1.5) were added. A polyacrylonitrile cloth was printed with the printing paste thus obtained. The print was dried, subjected to 30 minutes steaming and rinsed. A blue print having very good fastness was obtained.

It has been found that particularly preferred cationic azo dyestuffs of the present invention have the following formulas:

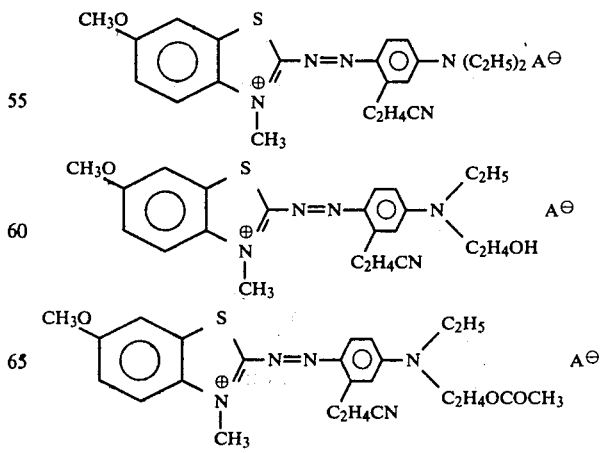

-continued

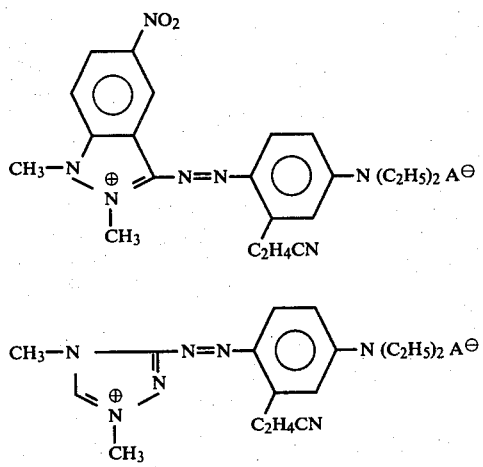

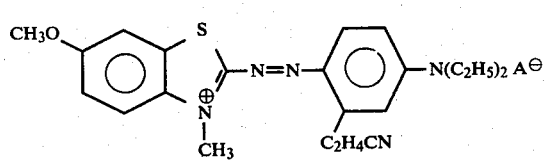

The foregoing dyestuffs correspond to Examples 1, 12, 13, 29 and 41 respectively.

What is claimed is:

1. Cationic azo dyestuff having the formula:

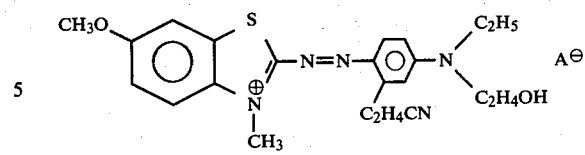

in which $A^\ominus$ represents an anion.

2. Cationic azo dyestuff having the formula:

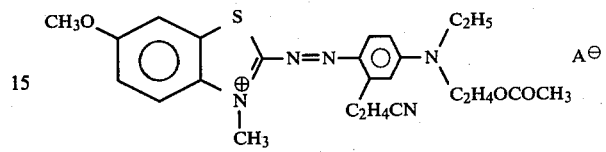

in which $A^\ominus$ represents an anion.

3. Cationic azo dyestuff having the formula:

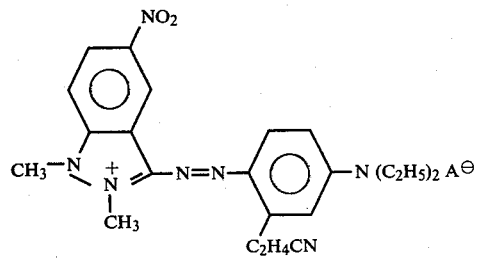

in which $A^\ominus$ represents an anion.

4. Cationic azo dyestuff having the formula:

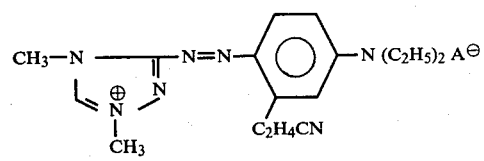

in which $A^\ominus$ represent an anion.

5. Cationic azo dyestuff having the formula:

in which $A^\ominus$ is an anion.

* * * * *